(12) United States Patent
Sako

(10) Patent No.: US 7,058,158 B2
(45) Date of Patent: Jun. 6, 2006

(54) X-RAY APPARATUS CAPABLE OF OPERATING IN A PLURALITY OF IMAGING MODES

(75) Inventor: Tsukasa Sako, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/219,115

(22) Filed: Sep. 2, 2005

(65) Prior Publication Data

US 2006/0050846 A1    Mar. 9, 2006

(30) Foreign Application Priority Data

Sep. 7, 2004  (JP) ............................. 2004-260113

(51) Int. Cl.
*A61B 6/00* (2006.01)
*H05G 1/56* (2006.01)

(52) U.S. Cl. ..................................... 378/17; 378/114

(58) Field of Classification Search ................ 378/17, 378/20, 208, 114, 115, 116
See application file for complete search history.

(56) References Cited

U.S. PATENT DOCUMENTS 4,173,720 A    11/1979  Geluk
4,472,822 A *  9/1984  Swift ........................... 378/10
6,152,598 A    11/2000 Tomisaki

FOREIGN PATENT DOCUMENTS

| JP | 10-201745 | 8/1998 |
|----|-----------|--------|
| JP | 11-137544 | 5/1999 |
| JP | 2003-250787 | 9/2003 |

* cited by examiner

*Primary Examiner*—Edward J. Glick
*Assistant Examiner*—Mona Sanei
(74) *Attorney, Agent, or Firm*—Canon U.S.A. Inc. IP Division

(57) ABSTRACT

An X-ray apparatus capable of performing both computerized tomography (CT) imaging and usual radiography imaging (usual imaging) can realize high definition even in the usual imaging. In the X-ray apparatus, for the usual imaging, since a chair serving as a supporting structure for supporting a subject on a rotatable table is not required, the chair is withdrawn from an imaging field. The usual imaging is controlled so as to be permitted when the supporting structure is withdrawn from the imaging field. For imaging a knee, for example, sliding the chair allows imaging keeping the knee being in the rotation center. Therefore, a wide variety of imaging operations can be realized with a single flat-panel sensor.

24 Claims, 4 Drawing Sheets

X-RAY APPARATUS CAPABLE OF OPERATING IN A PLURALITY OF IMAGING MODES

BACKGROUND OF THE INVENTION

1. Field of the Invention

The present invention relates to an X-ray apparatus including a rotatable table for rotating a subject and being capable of operating in a first imaging mode of performing X-ray imaging while the subject is rotated and a second imaging mode of performing X-ray imaging while the subject remains stationary.

2. Description of the Related Art

A cone-beam X-ray computerized tomography (CT) apparatus is schematically shown in FIG. 2A. In this apparatus, a rotatable table 1 is disposed between an X-ray tube 103 and a flat-panel sensor 101. A chair 2 is fixed on the rotatable table 1.

As shown in FIG. 2B, X-ray imaging is performed on a subject 102 sitting on the chair 2 while the rotatable table 1 is rotated. X-rays emitted from the X-ray tube 103 are absorbed and attenuated in the body of the subject 102. The transmitted X-rays are then detected by the flat-panel sensor 101. The subject 102 is rotated about its axis while a positional relationship between the X-ray tube 103 and the flat-panel sensor 101 is maintained, so that projected image data in one turn is obtained. The obtained projected image data is reconstructed, so that a tomographic image is obtained. Instead of rotating the subject by one turn, the X-ray tube 103 and the flat-panel sensor 101 may be moved.

Cone-beam CT apparatuses are disclosed in, for example, Japanese Patent Laid-Open Nos. 52-140286 (corresponding to U.S. Pat. No. 4,173,720) and 60-207041. Apparatuses for performing plain imaging using flat-panel sensors are disclosed in, for example, Japanese Patent Laid-Open No. 10-201745. Techniques for withdrawing a movable top board from an X-ray irradiation field in an apparatus using a flat-panel sensor are disclosed in, for example, Japanese Patent Laid-Open Nos. 11-137544 (corresponding to U.S. Pat. No. 6,152,598) and 2003-250787.

A flat-panel sensor is relatively expensive, so the purchase of multiple flat-panel sensors entails high cost. Therefore, it is desire that a single cone-beam CT apparatus perform both cone-beam CT imaging and usual radiography imaging (usual imaging). However, a conventional cone-beam CT apparatus cannot realize sufficient definition when performing the usual imaging because the chair 2, including a seat 3 and a backrest 4 and disposed on the rotatable table 1, is imaged in the resulting image.

For example, when the subject is human, as shown in FIG. 2B, the chair 2 is included in the irradiation field, and therefore, the chair 2 is imaged as a projected image in the resulting image. On the other hand, when performing the cone-beam CT imaging on, for example, a knee, the chair 2 on the rotation axis will be an obstacle because the knee must be placed at the rotation center.

SUMMARY OF THE INVENTION

The present invention provides an X-ray apparatus capable of operating in a usual imaging mode and a CT imaging mode can realize high-definition images even in the usual imaging mode.

According to a first aspect of the present invention, an X-ray apparatus capable of operating in a first imaging mode of performing X-ray imaging while a subject is rotated and a second imaging mode of performing X-ray imaging while the subject remains stationary includes a rotatable table for rotating the subject, a securing member for securing the subject, the securing member being disposed on the rotatable table, a moving unit configured to move the securing member between a position within an imaging field of the X-ray apparatus and a position outside the imaging field, a detecting unit configured to detect a position of the securing member, and a controlling unit configured to inhibit the apparatus from operating in the second imaging mode while the position of the securing member is detected to be present within the imaging field of the X-ray apparatus.

According to a second aspect of the present invention, an X-ray apparatus capable of operating in a first imaging mode of performing X-ray imaging while a subject is rotated and a second imaging mode of performing X-ray imaging while the subject remains stationary includes a rotatable table for rotating the subject, a rotation locking unit configured to lock the rotatable table so as to inhibit rotation of the rotatable table, a detecting unit configured to detect whether the rotation locking unit has locked the rotatable table so as to inhibit the rotatable table from being rotated, and a controlling unit configured to inhibit the apparatus from operating in the first imaging mode while the detecting unit detects that the rotatable table is locked so as not to be rotated.

Further features of the present invention will become apparent from the following description of exemplary embodiments (with reference to the attached drawings).

DESCRIPTION OF THE EMBODIMENTS

The embodiments are described below with reference to the drawings.

Figure 1:
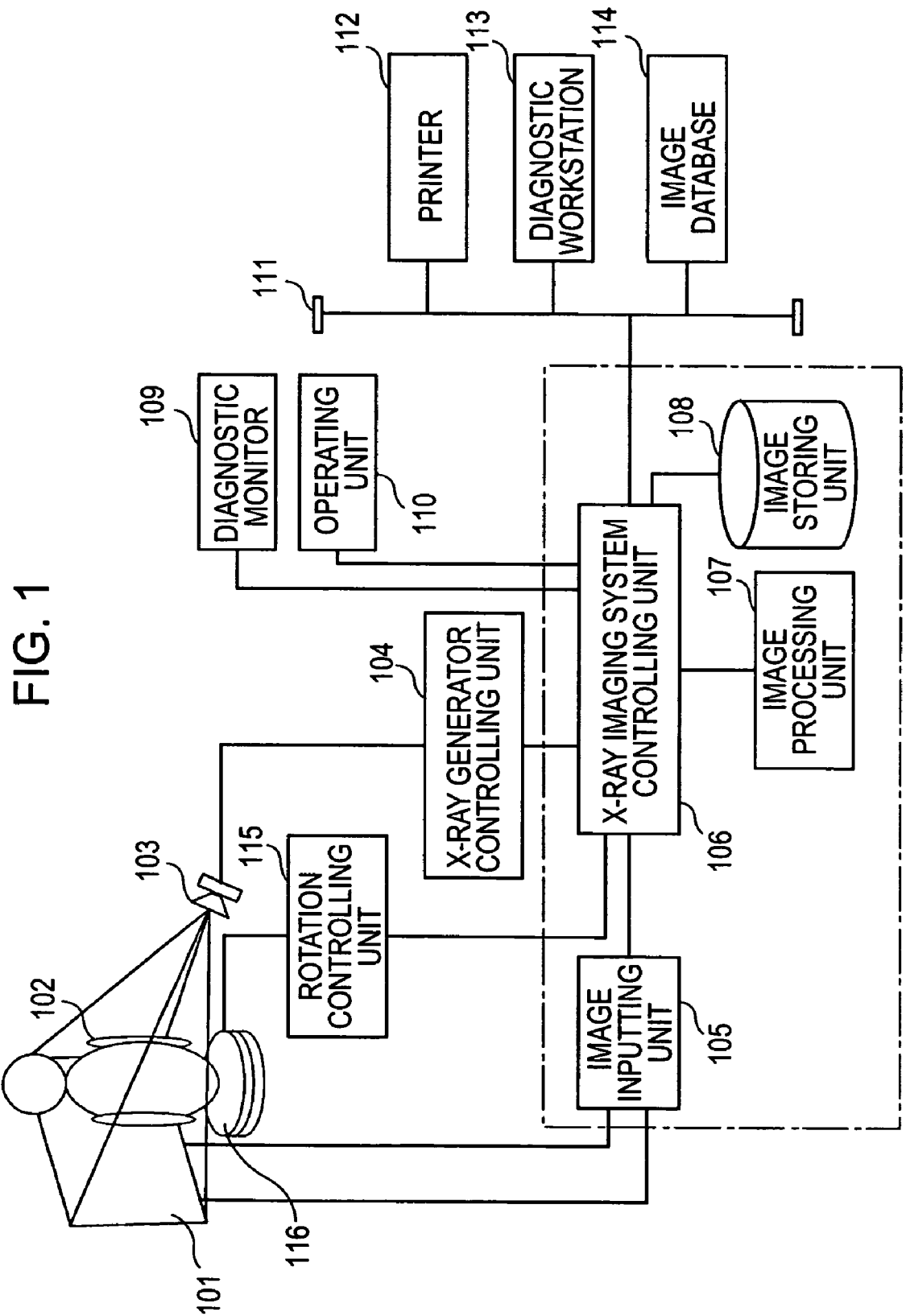
FIG. 1 shows the entire structure of a cone-beam X-ray CT apparatus according to an embodiment of the present invention.
Figure 2A:
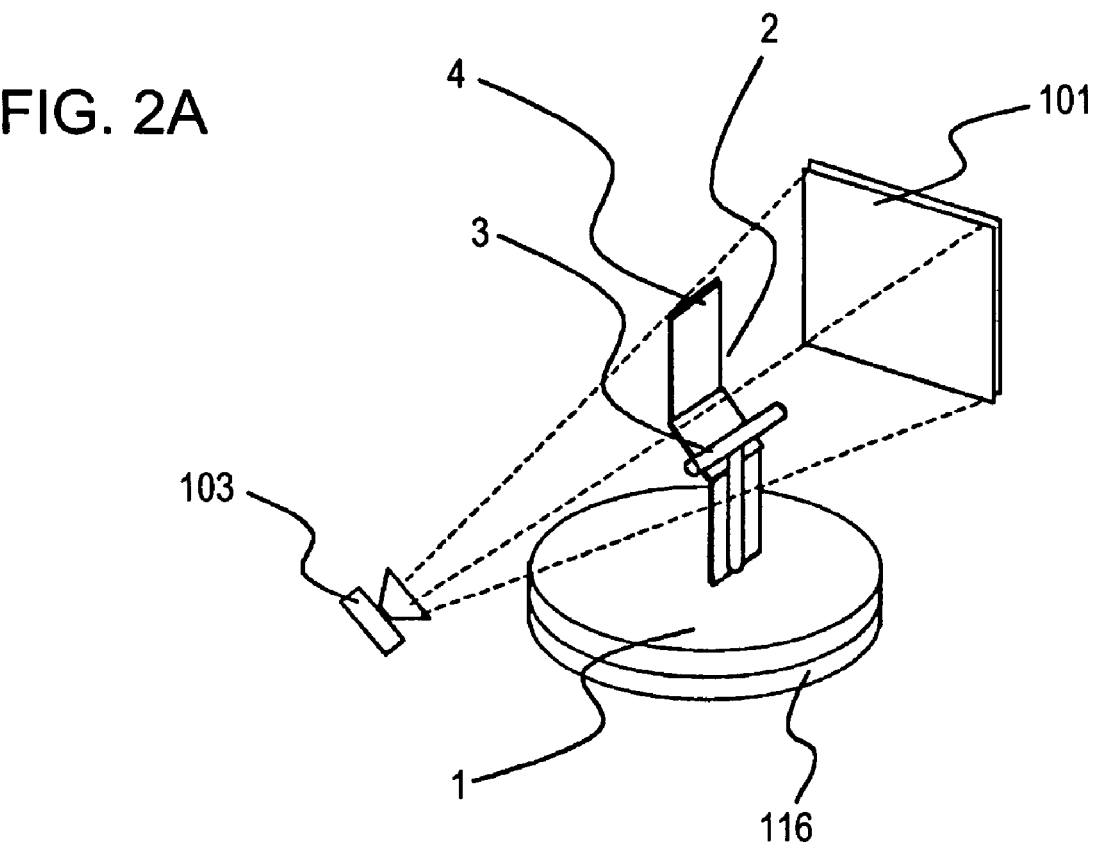
FIGS. 2A and 2B are schematic views of a cone-beam X-ray CT apparatus.
Figure 2B:
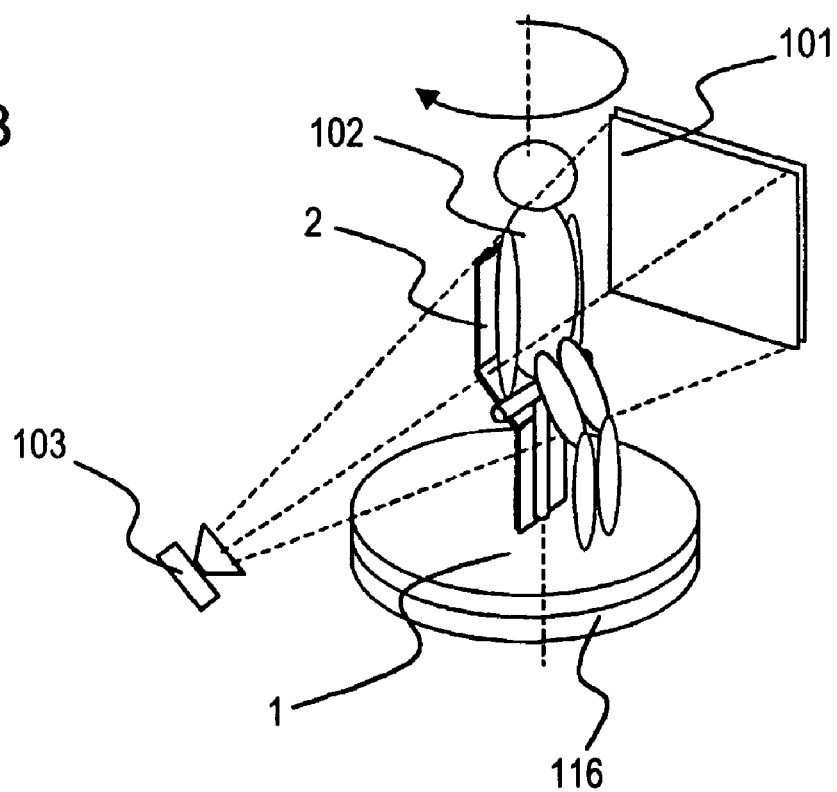

FIG. 1 is a block diagram schematically showing the entire structure of an X-ray apparatus according to an embodiment of the present invention.

An X-ray imaging system controlling unit 106 performs imaging control, image collection, image processing, and image outputting in the X-ray apparatus.

When the X-ray imaging system controlling unit 106 instructs an X-ray generator controlling unit 104 to generate X-rays, an X-ray source 103 controlled by the X-ray generator controlling unit 104 emits X-rays. The X-rays emitted from the X-ray source 103 pass through a subject 102 and are detected by an X-ray detector 101. The X-rays detected by the X-ray detector 101 are input as a projected image to an image inputting unit 105.

An operating unit 110 allows the imaging mode to be set. An operator of the X-ray apparatus selects the usual imaging mode or the CT imaging mode with the operating unit 110 before performing X-ray imaging. The term "usual imaging"

used herein represents X-ray imaging of a stationary subject, i.e., plain radiographic imaging.

For imaging in the CT imaging mode, the subject 102, which is fixed on a rotary base 116, is rotated while the relative positional relationship between the X-ray source 103 and the X-ray detector 101 is maintained.

The X-ray imaging system controlling unit 106 controls a rotation controlling unit 115, the X-ray generator controlling unit 104, the X-ray detector 101, and the image inputting unit 105, so that X-ray imaging of the subject 102 is continuously performed while the rotary base 116 is rotated. As a result, a projected image is obtained at each rotation angle of the rotary base 116. The structure of the rotary base 116 is described later.

An image processing unit 107 performs image processing, such as preprocessing, including correction of the X-ray detector 101 and log conversion, reconstruction, and the like, on input projected images from each rotation angle to create a set of tomograms.

The created set of tomograms is displayed on a diagnostic monitor 109, stored on an image storing unit 108, and/or output to a printer 112, to a diagnostic workstation 113, and/or to an image database 114 via a network 111.

Using the operating unit 110, an operator performs various operations, such as an operation relating to a window appearing on the diagnostic monitor 109, an operation of switching between the displayed tomograms in the body axis, an operation of reformatting images, an operation for three-dimensionally displaying images, and the like.

On the other hand, for imaging in the usual imaging mode, X-ray imaging of the subject 102 is performed while the rotary base 116 is controlled not to be rotated. In this mode the image processing unit 107 also performs image processing on the images obtained. The processed images are displayed on the diagnostic monitor 109.

More specifically, the X-ray imaging system controlling unit 106 controls the X-ray generator controlling unit 104, the X-ray detector 101, the rotation controlling unit 115, and the image inputting unit 105, so that X-ray imaging of the subject 102 is performed while the rotary base 116 remains stationary.

Figure 3:
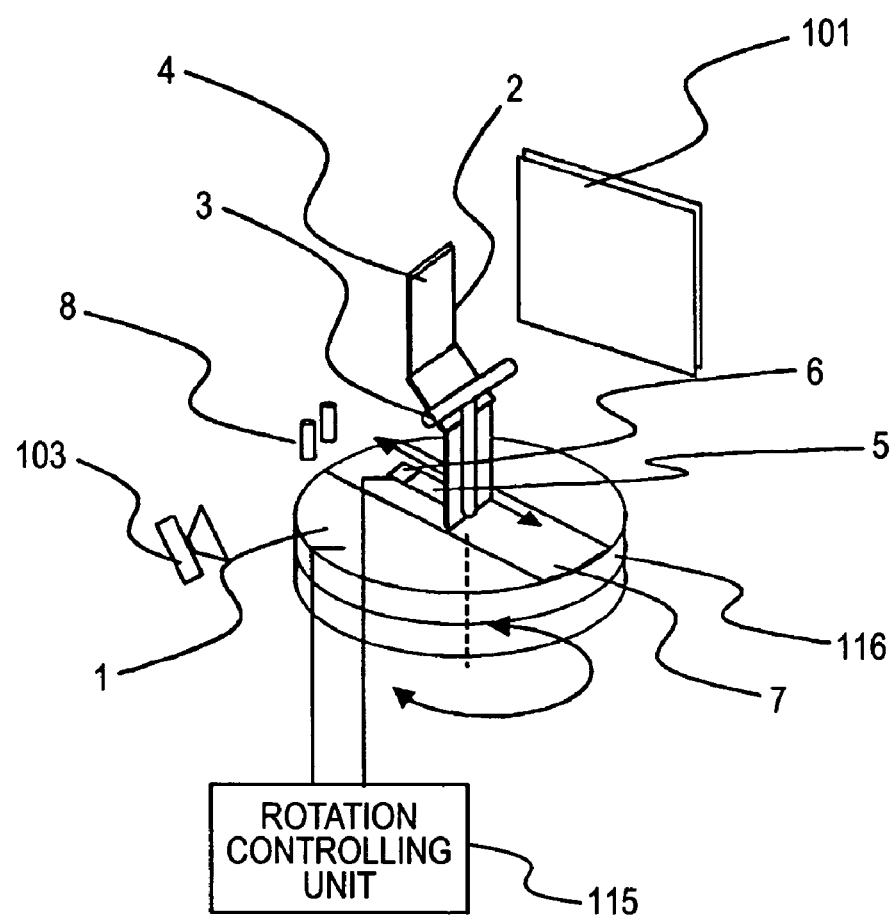
FIG. 3 is an illustration for explaining a rotary base.

FIG. 3 is a schematic diagram showing the rotary base 116.

The rotary base 116 is disposed between the X-ray source 103 and the X-ray detector 101. The rotary base 116 has a rotatable table 1 on which a chair 2, including a seat 3 and a backrest 4, is disposed. The chair 2 serves as a securing member for securing the subject 102 on the rotary base 116. The chair 2 further has a stopper tongue portion 5 and a stopper detection portion 6. The chair 2 is movable between a position within an X-ray irradiation path (imaging field), which is shown in "A" in FIGS. 4 and 5, defined by the X-ray source 103 and the X-ray detector 101 and a position outside the X-ray irradiation path (imaging field) by sliding along a guide 7 of the rotatable table 1. The chair 2 is allowed to slide along the guide 7 of the rotatable table 1 when the rotatable table 1 is in a predetermined position. The guide 7 serves as a moving unit for the chair 2, but other arrangements for moving the chair 2 are possible. The position shown in FIG. 5 outside the irradiation path (imaging field) corresponds to a state in which the rotatable table 1 is in the predetermined position.

A stopper 8 is implanted in the floor on which the rotary base 116 is placed. The stopper 8 and the stopper tongue portion 5 engage with each other when the chair 2 is moved up to a position away from the X-ray irradiation path. The rotation controlling unit 115 controls the rotation of the rotatable table 1 by controlling a motor (not shown), and additionally, when the chair 2 is moved to up to the position away from the X-ray irradiation path, the stopper tongue portion 5 engages with the stopper 8, thus locking the rotatable table 1 so as not to be rotated (the tongue 5 thus providing a rotation locking unit). When the stopper tongue portion 5 engages with the stopper 8, the stopper detection portion 6 detects the engagement of the stopper tongue portion 5 with the stopper 8. In other words, when the chair 2 is slid along the guide 7 up to the position away from the X-ray irradiation path so that the stopper tongue portion 5 and the stopper 8 engage with each other, the rotation of the rotatable table 1 is inhibited and the stopper detection portion 6 detects that the chair 2 lies in the position away from the X-ray irradiation path.

The imaging operation is described below.

First, the imaging mode is set with the operating unit 110 before X-ray imaging is performed. In this case, the usual imaging mode or the CT imaging mode can be set.

Figure 4:
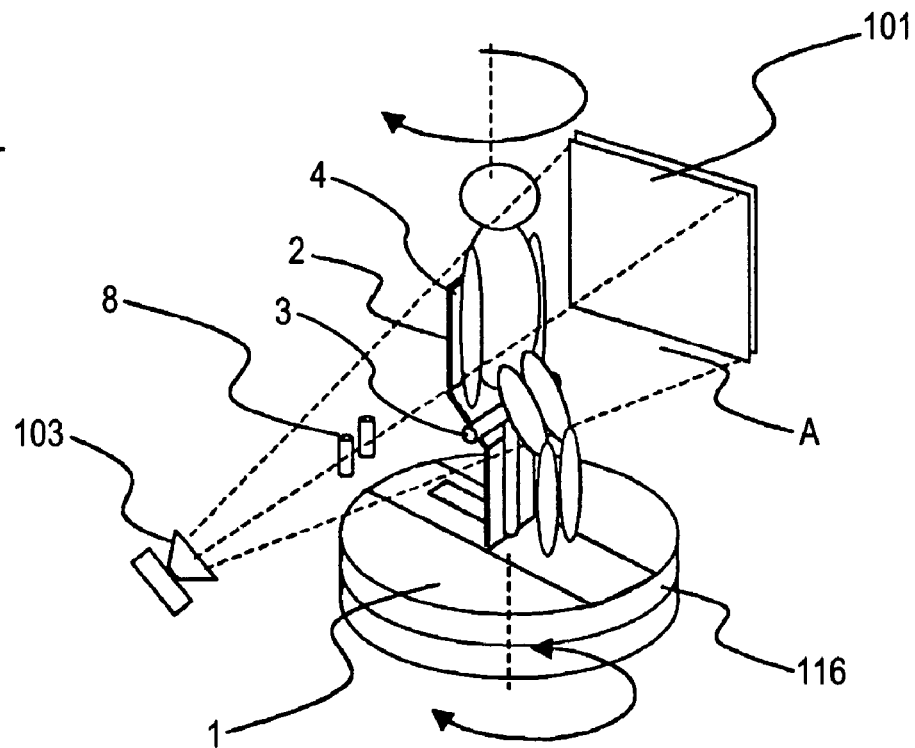
FIG. 4 is an illustration for explaining chest imaging in the CT imaging mode.

FIG. 4 shows how to perform chest imaging in the CT imaging mode. In the CT imaging mode, it is necessary to secure the subject 102 as much as possible while the rotatable table 1 is rotated a half or one turn. Therefore, the attitude of the subject 102 is secured using the seat 3 and the backrest 4.

Figure 5:
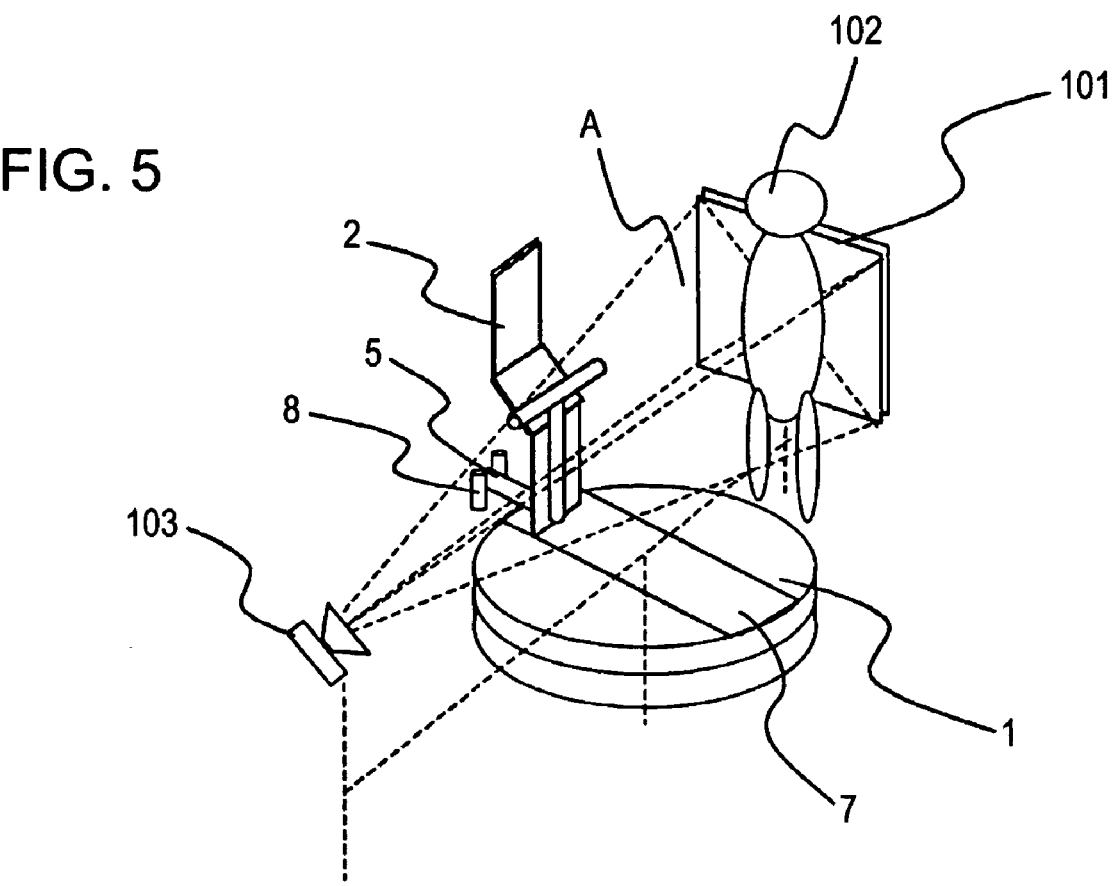
FIG. 5 is an illustration for explaining frontal chest imaging in the usual imaging mode.

FIG. 5 shows how to perform frontal chest imaging in the usual imaging mode. In FIG. 5, after the chair 2 in the state shown in FIG. 4 is slid along the guide 7, the chair 2 lies in a position outside the X-ray irradiation path, and the stopper tongue portion 5 and the stopper 8 engage with each other. The engagement of the stopper tongue portion 5 with the stopper 8 inhibits the rotatable table 1 from being rotated.

The X-ray imaging system controlling unit 106 controls the X-ray generator controlling unit 104, the X-ray detector 101, and the image inputting unit 105 so that imaging in the usual imaging mode can be performed in a state in which the engagement of the stopper tongue portion 5 with the stopper 8 is detected by the stopper detection portion 6. In this state the X-ray imaging system controlling unit 106 inhibits images from being made in the CT imaging mode. In the case where the stopper detection portion 6 does not detect the engagement, the X-ray imaging system controlling unit 106 controls the X-ray generator controlling unit 104 and the X-ray detector 101 so that imaging in the usual imaging mode cannot be performed.

Such a control system is carried out to avoid poor definition, which may cause inaccurate diagnosis, resulting from a phenomenon in which the chair 2 is imaged in an X-ray image by accidentally imaging the subject 102 when the chair 2 lies within the X-ray irradiation path.

In the apparatus according to the embodiment, however, this control system can be enabled or disabled. In the case when the control system is disabled, imaging in the usual imaging mode can be performed regardless of the presence or absence of the detection performed by the detecting structure. If imaging in the usual imaging mode is accidentally performed, it is necessary to simply perform imaging again.

In the CT imaging mode, various subjects can be imaged, in addition to the chest. For example, a knee can be subjected to imaging. However, if imaging is performed in the state shown in FIG. 4, the knee would be moved off the rotation center of the rotatable table 1 because the chair 2 lies at the rotation center.

Figure 6:
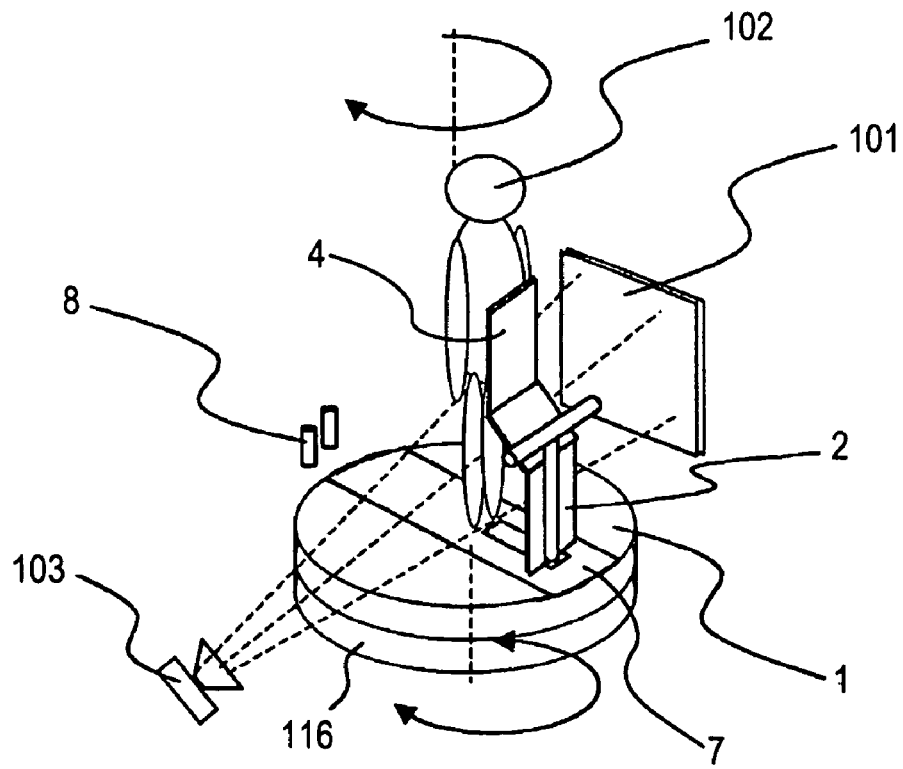
FIG. 6 is an illustration for explaining cone-beam CT imaging of a knee.

To deal with such a case, as shown in FIG. 6, for example, imaging can be performed after the chair 2 is moved along the guide 7 in a direction opposite to that of FIG. 5 and the chair 2 is then secured so that the subject 102 can lean against the back of the backrest 4 so as to keep the knee being in the rotation center.

According to the embodiment described above, for imaging in the usual imaging mode requiring higher definition, the chair 2 is inhibited from being imaged in the resulting image. For the cone-beam CT imaging, the required definition is less than that for the usual imaging, and holding the subject 102 in place is more important. Therefore, it does not much matter if the chair 2 is imaged in the resulting image.

In the embodiment described above, fixing the stopper tongue portion 5 with the stopper 8 inhibits the rotatable table 1 from being rotated. Alternatively, the rotation controlling unit 115 may control the rotatable table 1 not to be rotated by detecting the position of the chair 2 on the guide 7 with a first linear encoder, detecting the rotation angle of the rotatable table 1 with a second linear encoder, and increasing a fastening torque of the motor for rotating the rotatable table 1 when the detected values are within respective predetermined ranges. This provides an alternative form of a rotation locking unit.

In the embodiment described above, the chair 2 can be horizontally moved up to a position away from the X-ray irradiation path. Alternatively, the rotatable table 1 may be, for example, vertically movable so that the chair 2 can be vertically moved up to a position away from the X-ray irradiation path. This structure realizes the same advantages.

The embodiment can be realized by, for example, the execution of a program by a computer. Means for supplying the program to the computer, for example, a computer-readable storage medium storing the program, such as a compact disk read-only memory (CD-ROM), and transmission media for transmitting the program, such as the Internet, are applicable as one embodiment of the present invention. The program itself is applicable as another embodiment of the present invention. The program, the storage medium, the transmission medium, and the program product are included in the scope of the present invention.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions.

This application claims the benefit of Japanese Application No. 2004-260113 filed Sep. 7, 2004, which is hereby incorporated by reference herein in its entirety.

What is claimed is:

1. An X-ray apparatus capable of operating in a first imaging mode of performing X-ray imaging while a subject is rotated and a second imaging mode of performing X-ray imaging while the subject remains stationary, the X-ray apparatus comprising:
   a rotatable table for rotating the subject;
   a securing member for securing the subject, the securing member being disposed on the rotatable table;
   a moving unit configured to move the securing member between a position within an imaging field of the X-ray apparatus and a position outside the imaging field;
   a detecting unit configured to detect a position of the securing member; and
   a controlling unit configured to inhibit the apparatus from operating in the second imaging mode while the position of the securing member is detected to be present within the imaging field of the X-ray apparatus.

2. The X-ray apparatus according to claim 1, wherein the controlling unit inhibits the apparatus from operating in the first imaging mode while the position of the securing member is detected to be present outside the imaging field.

3. The X-ray apparatus according to claim 1, further comprising a rotation locking unit configured to lock the rotatable table so as to inhibit rotation of the rotatable table when the securing member is moved up to the position outside the imaging field of the X-ray apparatus with the moving unit.

4. The X-ray apparatus according to claim 2, further comprising a rotation locking unit configured to lock the rotatable table so as to inhibit rotation of the rotatable table when the securing member is moved up to the position outside the imaging field of the X-ray apparatus with the moving unit.

5. The X-ray apparatus according to claim 1, further comprising:
   a rotation locking unit including a protrusion portion that protrudes from an outer dimension of the rotatable table when the securing member is moved by the moving unit up to the position outside the imaging field of the X-ray apparatus, the rotation locking unit being configured to lock the rotatable table so as to inhibit rotation of the rotatable table by engaging the protrusion portion with a stopper.

6. The X-ray apparatus according to claim 2, further comprising:
   a rotation locking unit including a protrusion portion that protrudes from an outer dimension of the rotatable table when the securing member is moved by the moving unit up to the position outside the imaging field of the X-ray apparatus, the rotation locking unit being configured to lock the rotatable table so as to inhibit rotation of the rotatable table by engaging the protrusion portion with a stopper.

7. The X-ray apparatus according to claim 3, further comprising:
   a rotation locking unit including a protrusion portion that protrudes from an outer dimension of the rotatable table when the securing member is moved by the moving unit up to the position outside the imaging field of the X-ray apparatus, the rotation locking unit being configured to lock the rotatable table so as to inhibit rotation of the rotatable table by engaging the protrusion portion with a stopper.

8. The X-ray apparatus according to claim 4, further comprising:
   a rotation locking unit including a protrusion portion that protrudes from an outer dimension of the rotatable table when the securing member is moved by the moving unit up to the position outside the imaging field of the X-ray apparatus, the rotation locking unit being configured to lock the rotatable table so as to inhibit rotation of the rotatable table by engaging the protrusion portion with a stopper.

9. The X-ray apparatus according to claim 1, further comprising:
   a rotation controlling unit configured to control rotation of the rotatable table,
   wherein the rotation controlling unit is configured to apply a fastening torque to the rotatable table when the position of the securing member is detected to be present outside the imaging field of the X-ray apparatus.

10. The X-ray apparatus according to claim 2, further comprising:
    a rotation controlling unit configured to control rotation of the rotatable table, wherein the rotation controlling unit is configured to apply a fastening torque to the rotatable table when the position of the securing member is detected to be present outside the imaging field of the X-ray apparatus.

11. The X-ray apparatus according to claim 3, further comprising:

a rotation controlling unit configured to control rotation of the rotatable table, wherein the rotation controlling unit is configured to apply a fastening torque to the rotatable table when the position of the securing member is detected to be present outside the imaging field of the X-ray apparatus.

12. The X-ray apparatus according to claim 4, further comprising:

a rotation controlling unit configured to control rotation of the rotatable table, wherein the rotation controlling unit is configured to apply a fastening torque to the rotatable table when the position of the securing member is detected to be present outside the imaging field of the X-ray apparatus.

13. The X-ray apparatus according to claim 1, further comprising:

a reconstructing unit configured to reconstruct a plurality of images imaged in the first imaging mode.

14. The X-ray apparatus according to claim 13, further comprising:

a display unit configured to display an image reconstructed by the reconstructing unit.

15. The X-ray apparatus according to claim 1, further comprising:

an image processing unit configured to perform image processing on an image imaged in the second imaging mode.

16. The X-ray apparatus according to claim 15, further comprising:

a display unit configured to display an image processed by the image processing unit.

17. The X-ray apparatus according to claim 1, wherein the moving unit allows the securing member to move beyond the center of rotation of the table in a direction opposite to a direction toward the position outside the imaging field.

18. An X-ray apparatus capable of operating in a first imaging mode of performing X-ray imaging while a subject is rotated and a second imaging mode of performing X-ray imaging while the subject remains stationary, the X-ray apparatus comprising:

a rotatable table for rotating the subject;

a rotation locking unit configured to lock the rotatable table so as to inhibit rotation of the rotatable table;

a detecting unit configured to detect whether the rotation locking unit has locked the rotatable table so as to inhibit the rotatable table from being rotated; and a controlling unit configured to inhibit the apparatus from operating in the first imaging mode while the detecting unit detects that the rotatable table is locked so as not to be rotated.

19. The X-ray apparatus according to claim 18, further comprising:

a reconstructing unit configured to reconstruct a plurality of images imaged in the first imaging mode.

20. The X-ray apparatus according to claim 19, further comprising:

a display unit configured to display an image reconstructed by the reconstructing unit.

21. The X-ray apparatus according to claim 18, further comprising:

an image processing unit configured to perform image processing on an image imaged in the second imaging mode.

22. The X-ray apparatus according to claim 19, further comprising:

an image processing unit configured to perform image processing on an image imaged in the second imaging mode.

23. The X-ray apparatus according to claim 20, further comprising:

an image processing unit configured to perform image processing on an image imaged in the second imaging mode.

24. The X-ray apparatus according to claim 21, further comprising:

a display unit configured to display an image processed by the image processing unit.

* * * * *